(12) United States Patent
Swank et al.

(10) Patent No.: US 7,549,349 B2
(45) Date of Patent: Jun. 23, 2009

(54) SAMPLE CARTRIDGE FOR AIR-SAMPLING DEVICE

(75) Inventors: Freeman Swank, Olathe, KS (US); Christopher Tesluk, Kansas City, MO (US)

(73) Assignee: Evogen, Inc., Kansas City, MO (US)

( * ) Notice: Subject to any disclaimer, the term of this patent is extended or adjusted under 35 U.S.C. 154(b) by 348 days.

(21) Appl. No.: 11/426,004

(22) Filed: Jun. 22, 2006

(65) Prior Publication Data

US 2007/0295112 A1    Dec. 27, 2007

(51) Int. Cl.
  *G01N 1/20*  (2006.01)
  *G01N 1/22*  (2006.01)
(52) U.S. Cl. .................. 73/863.71; 73/864
(58) Field of Classification Search .......... 73/863.71, 73/64.56, 53.01, 864; 435/5, 7.2, 7.21, 286.6–288.7
See application file for complete search history.

(56) References Cited

U.S. PATENT DOCUMENTS

| 4,957,706 A | 9/1990 | Romette et al. ............. 422/100 |
| 5,538,690 A | 7/1996 | Greer et al. .................... 422/86 |
| 5,550,059 A | 8/1996 | Boger et al. .................. 436/54 |
| 6,082,185 A * | 7/2000 | Saaski ........................ 73/64.56 |
| 6,391,541 B1 | 5/2002 | Petersen et al. ................ 435/5 |
| 6,656,428 B1 | 12/2003 | Clark et al. .................... 422/58 |
| 6,713,298 B2 | 3/2004 | McDevitt et al. ......... 435/287.8 |
| 2002/0042125 A1* | 4/2002 | Petersen et al. .......... 435/287.2 |
| 2003/0170881 A1* | 9/2003 | Davis et al. .............. 435/287.2 |

OTHER PUBLICATIONS

International Search Report and Written Opinion for PCT/US07/14555 dated Nov. 13, 2007 (10 pages).

* cited by examiner

*Primary Examiner*—Hezron Williams
*Assistant Examiner*—Tamiko D Bellamy
(74) *Attorney, Agent, or Firm*—Polsinelli Shugart

(57) ABSTRACT

The present invention provides a sample cartridge for use with an air and gas sampling device. The cartridge includes a body that defines an interior space, a top portion attached to the body and substantially covering the interior space, and first and second valves seated in the top portion of the cartridge. The valves automatically seal to prevent leakage from the cartridge when the cartridge is not in operable position within the air and gas sampling device.

32 Claims, 4 Drawing Sheets

SAMPLE CARTRIDGE FOR AIR-SAMPLING DEVICE

CROSS-REFERENCE TO RELATED APPLICATIONS

Not Applicable.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

BACKGROUND OF THE INVENTION

The present invention relates generally to chemical and biological sampling, and more specifically to a self-sealing sample cartridge for use with a device for monitoring ambient air or other gas for chemical or biological compounds.

Systems for real-time detection of biological and chemical compounds or agents are known in the art. Exemplary known systems may utilize a contactor having a substrate therein, such that the air or gas being analyzed comes into contact with the substrate, such as water, so that chemical and biological compounds or agents are transferred thereto.

Such devices may have a number of limitations. For example, known devices may utilize a sample container that is not removable from the device but is, instead, an integral component thereof. This makes cleaning of the sample container difficult. Further, even if the sample container is removable, it may be a permanent part of the device, being used over multiple sampling runs throughout the life of the device. This increases the chances that the sample container will suffer from cross-contamination between runs, from being generally dirty, or from ordinary wear and tear to the device during use. Further, such sample containers may become prone to leakage due to weakening seals or other portions of the container structure with reuse over time. It is therefore desirable to provide a self-sealing, single-use sample cartridge for use with a gas or air monitoring device, such that the cartridge is not susceptible to cross-contamination or dirtying due to repeated use, and is not susceptible to structural weakening due to repeated use over time.

A further problem with some known air and gas monitoring devices is that, upon initial use, the device must provide fluid from a fluid reservoir into the device so that the fluid can be delivered to a contactor, where it acts as a substrate during the sampling run. The process of delivering fluid from a reservoir, through the device, to a contactor takes time and can lead to slow startup times for the sampling device. Thus, it is desirable to provide a component to such a device that allows for rapid startup of the device. Further, in some known devices, the use of a pressure-based fluid level control would require a component that maintains a pressure seal at its machine interface.

Further, in known devices, collection and storage of a sample after a sampling run may require transfer of the sample to a storage container external to the device, such as by manual transfer at the hands of a technician or other skilled worker. This allows opportunity for contamination of the sample during transfer, or due to contamination of the storage receptacle. It also presents the possibility of exposure of the technician to harmful chemicals or agents within the sample.

An additional problem presented by devices that require transfer of the collected sample to a storage container is that the storage container may be mislabeled or may contain insufficient data to identify the sample and the parameters of the sampling run from which the sample was obtained. This can lead to faulty interpretation of data taken from analysis of the sample, or in some cases may render the sample useless for further analysis. Thus, it is desirable to provide a sample storage container for any given sample within the sampling device itself, and likewise to provide a unique identifier for any given sample. Likewise, it is further desirable to provide an automatic means of imparting identification information to the sample storage container upon delivery of the sample to the container.

Further, in known devices it is typically required that the collected sample be pretreated with buffer solutions, biochemical assays, or other chemicals that are used as part of the analysis method. Thus it is desirable to provide a sample storage container that is pre-filled with the required chemicals for analysis.

BRIEF SUMMARY OF THE INVENTION

The present invention provides a sample cartridge for use with an air and gas sampling device. The cartridge includes a body that defines an interior space, a top portion attached to the body and substantially covering the interior space, and a plurality of valves seated in the top portion of the cartridge. The present invention preferably uses three or four valves. The valves automatically seal to prevent leakage from the cartridge when the cartridge is not in operable position within the air and gas sampling device. It is preferred that the valves deform when the present cartridge is installed in an air and gas sampling device, thereby allowing unrestricted fluid flow in and out of the cartridge.

In another aspect of the present invention, a lid portion is provided, the lid being engageable with the top portion of the cartridge. When the lid is closed, it forms a seal against the valves. The lid portion may be fixedly attached to the body portion, such as by a hinge, or may be entirely removable from the body.

In another aspect of the invention, gripping features are provided to allow the user to insert and remove the cartridge from the air sampling device.

In another aspect of the present invention, the sample cartridge is provided with a data storage portion for storing data related to the cartridge or to the sample stored within the cartridge. The data storage portion may be a magnetic storage device, a flash storage device, a computer-readable disc, a RAM storage device, a radio frequency identification device (RFID), a combination of these, or any other suitable data storage device, and may be interfaced with remotely or by direct connection to the present invention.

In yet another aspect of the present invention, the sample cartridge is provided with a data receiver for receiving data transmitted from the air and gas sampling device or from some other source external to the sample cartridge.

In another aspect of the invention, the sample cartridge is provided with buffers, biochemical markers, or other chemicals that aid in analysis of the sample.

In still another aspect of the present invention, the sample cartridge is provided with a data transmitter for transmitting data to the air and gas sampling device or to some other external receiver.

In another aspect of the present invention, the sample cartridge is a single-use, disposable cartridge.

DETAILED DESCRIPTION OF THE INVENTION

Figure 1:
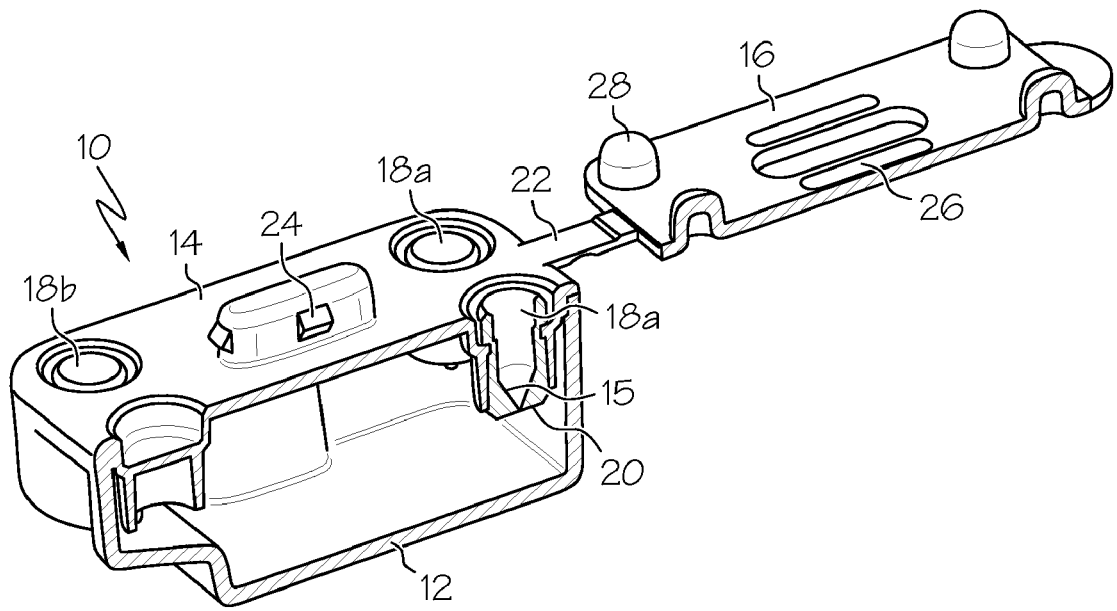
FIG. 1 is a cross-section of a perspective view of a sample cartridge according to the present invention, the sample cartridge having a cap portion in the open position.

According to the principles of the present invention, a self-sealing sample cartridge is provided for use with an air and gas sampling device. The cartridge is used to provide an initial fluid charge to a contactor of the air and gas sampling device, as well as to accept and provide additional fluid during a sampling run and to serve as a final sample storage container after the completion of a sampling run. The cartridge also serves as an air pressure bridge during operation, and a vacuum reservoir during sample extraction. In one aspect of the present invention, the sample cartridge is a single-use cartridge.

Turning now to the drawings, wherein like numerals represent like parts, the numeral 10 refers generally to a sample cartridge constructed in accordance with the teachings of the present invention. Sample cartridge 10 includes a body 12, a top portion 14, a cap 16, and first, second and third valves 18a, 18b, and 18c. A position for a fourth valve 18d, described below, is preferably also provided, but is sealed in the embodiment of the present invention shown in the drawings. These and other features of sample cartridge 10 are described more fully below.

Sample cartridge 10 has multiple functions when used in conjunction with a device or system for monitoring the ambient air or other gases. When first installed for use in a gas and air sampling device, sample cartridge 10 preferably contains a volume of fluid that acts as the initial collection fluid charge. This initial fluid charge is delivered to a contactor of the air and gas sampling device when a collection cycle is commenced. The sample cartridge also acts as a fluid level maintenance reservoir during a collection run, when the air and gas monitoring device is collecting particles from samples of the air or other gas being monitored. Thus, fluid contained within sample cartridge 10 is delivered to the contactor of the air and gas sampling device over the course of the sampling run. Fluid from an external source may be added to the cartridge during a run, and air pressure may be introduced to the cartridge to affect the rate and direction of fluid transfer to or from the cartridge. Finally, sample cartridge 10 also acts as the final sample collection vessel at the end of a collection run. When the collection run is ended, air pressure in the cartridge is reduced to transfer fluid from the contactor of the air and gas sampling device to the sample cartridge 10 for storage or further processing. The fourth valve position 18d allows fluid in the cartridge to be drawn out while the cartridge is mounted in the air and gas sampling device, for use by internal analysis or archival devices. Further, the fourth valve position allows for the cartridge to be used for multiple samples while preserving the ability to replace the cartridge quickly and easily.

As shown in FIG. 1, body 12 and top portion 14 are preferably welded together or otherwise hermetically sealed. Alternatively, sample cartridge 10 may be produced such that body 12 and top portion 14 are constructed from a single, integral piece of material. Any manner of check valve may be used that restricts flow in one direction and can be mechanically opened to allow for flow in two directions. First, second, and third valves 18a, 18b, and 18c are pressed into top portion 14, and each preferably includes a duck-bill type seal 15 that remains closed until sample cartridge 10 is inserted into the ambient air and gas monitoring device with which it is being used. First, second, and third valves 18a, 18b, and 18c are preferably opened upon insertion into the air and gas monitoring device by a structure within the device itself that holds valves 18a, 18b, and 18c in open positions. For example, the air and gas monitoring device may include pins on a manifold (an example of which is described more fully below) that serve to open valves 18a, 18b, and 18c when sample cartridge 10 is placed in operating position prior to use of the sampling device. Once sample cartridge 10 is removed from the sampling device, valves 18a, 18b, and 18c close, for example, by the action of molded ribs 20, which serve to force the closure of the valves. Once valves 18a, 18b and 18c are closed, a seal is created such that collection fluid is prevented from leaking out of sample cartridge 10, thereby preventing the exposure of the user to contaminated fluid, and other fluids are prevented from entering sample cartridge 10 and contaminating the fluid therein.

Cap 16 is preferably molded as part of top portion 14, connected to top 14 by a molded hinge 22. When cap 16 is closed, cap 16 is held in place by detents 24, which interface with slots 26 to allow cap 16 to snap into place. This method of securely closing cap 16 allows for repeated opening and closing of cap 16 without loss of performance over time, and also allows for secure shipping and other handling of sample cartridge 10 without leakage of fluid therein or damage to valves 18a, 18b, and 18c. Cap 16 is sealed to top portion 14 of sample cartridge 10 by interference between sealing bosses 28 in cap 16 and the receiving geometry of valves 18a, 18b, and 18c. Although as shown in the figures, cap 16 is molded as an integral part of top portion 14, it is contemplated that cap 16 and top portion 14 may be provided as two separate portions.

Figure 2:
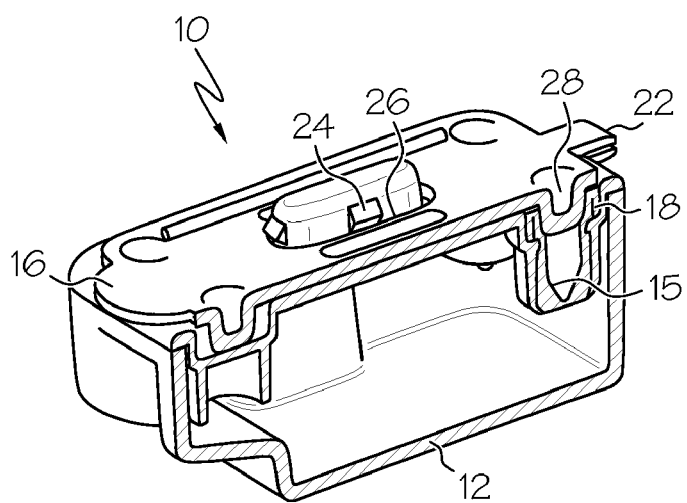
FIG. 2 is a cross-section of a perspective view of a sample cartridge according to the present invention, the sample cartridge having a cap portion in the closed position.

FIG. 2 depicts a cross-sectional view of a sample cartridge 10 constructed in accordance with the teachings of the present invention, sample cartridge 10 being shown with cap 16 in a closed position. With cap 16 in a closed position, sealing bosses 28 mate with the receiving geometry of valves 18a, 18b, and 18c to seal sample cartridge 10, such that fluid does not leak from sample cartridge 10 and fluid contained within sample cartridge 10 is not contaminated by particles or fluid from sources external to sample cartridge 10. With cap 16 in a closed position, sample cartridge 10 may be shipped or otherwise transported or handled without loss of fluid from within sample cartridge 10, and without risk to the user due to contact with the contents thereof. Further, the outer surface of cap 16 may be textured to better accept identification markings applied by the user with pen or other suitable means.

While sample cartridge 10 may be constructed as described above, with first, second, and third valves 18a, 18b, and 18c, sample cartridge 10 may also be provided as shown in FIGS. 1 and 2 with a fourth valve as indicated above. Alternatively, sample cartridge 10 may be provided with only two valves 18a and 18b. In such an embodiment of the present invention, one of valves 18a or 18b serves to allow fluid to flow along a sample line, while the other of valves 18a or 18b serves as a pressure connector between the cartridge and a contactor of a gas and air sampling device. One of valves 18a or 18b may further include the capacity to inject water into the system.

Figure 3:
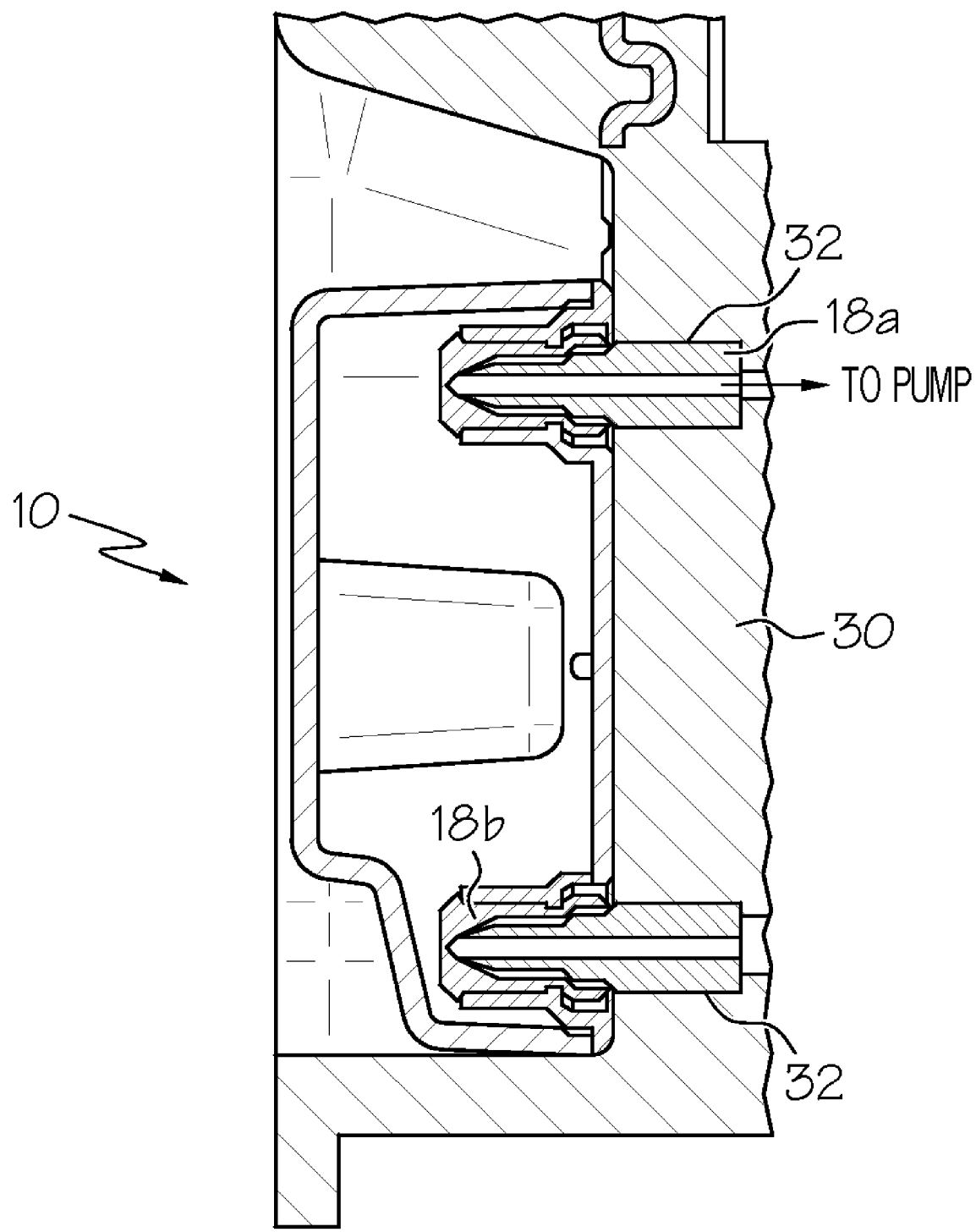
FIG. 3 is a cross-section view of a portion of an exemplary air and gas sampling device having a sample cartridge according to the present invention placed in operable position therein.

FIG. 3 depicts sample cartridge 10 as installed in an air and gas sampling device. Manifold 30 of the air and gas sampling device shown in the figures includes pins 32 that interface with first, second, and third valves 18a, 18b, and 18c, holding them open. The receiving geometry of first, second, and third valves 18a, 18b, and 18c is preferably such that a seal is formed between valves 18 and pins 32. Once first and second valves 18 are opened by pins 32, valves 18a, 18b, and 18c are in bidirectional liquid communication with manifold 30, and thus in communication with the air and gas sampling device.

As shown in FIG. 3, sample cartridge 10 is oriented in a vertical position when used in the exemplary air and gas monitoring device depicted in the drawings. When used in other such devices, sample cartridge 10 may have other orientations, including a horizontal orientation. Likewise, the size, shape, and overall configuration of sample cartridge 10 may differ from that shown in the drawings when sample cartridge 10 is used with other than the exemplary air and gas sampling device shown in the drawings. Further, the placement and configuration of valves 18 may vary. So long as the basic functionality of sample cartridge 10, as described herein, is preserved, the physical shape and configuration may be altered to meet the requirements of a specific sampling device or sampling application.

When sample cartridge 10 is first inserted into an air and gas sampling device, the sample cartridge preferably contains enough fluid to initially charge a contactor 42 (best seen in FIG. 4) of the air and gas sampling device. An air space encompasses two upper manifold pins 32 (one of which is visible in FIG. 3, the other, not visible, being positioned adjacent the first). One of upper manifold pins 32 is preferably in fluid communication with an air space within contactor 42 of the air and gas sampling device, a pump (not shown) that can draw a vacuum on the cartridge or can extract excess fluid from the cartridge, as well as with valve 18c of sample cartridge 10. The other upper manifold pin 32 is in fluid communication, via manifold 30, with a pump (not shown) that can charge sample cartridge 10 with a gas or liquid, as well as with valve 18a of sample cartridge 10. Lower manifold pin 32 is in fluid communication with the bottom of contactor 42 of the air and gas sampling device, as well as with valve 18b of sample cartridge 10. When a collection cycle is initiated, the pump in communication with one of upper manifold pins 32 pressurizes the cartridge, which pushes fluid through lower manifold pin 32 and into contactor 42 of the sampling device. This allows for a rapid startup of the device.

Figure 4:
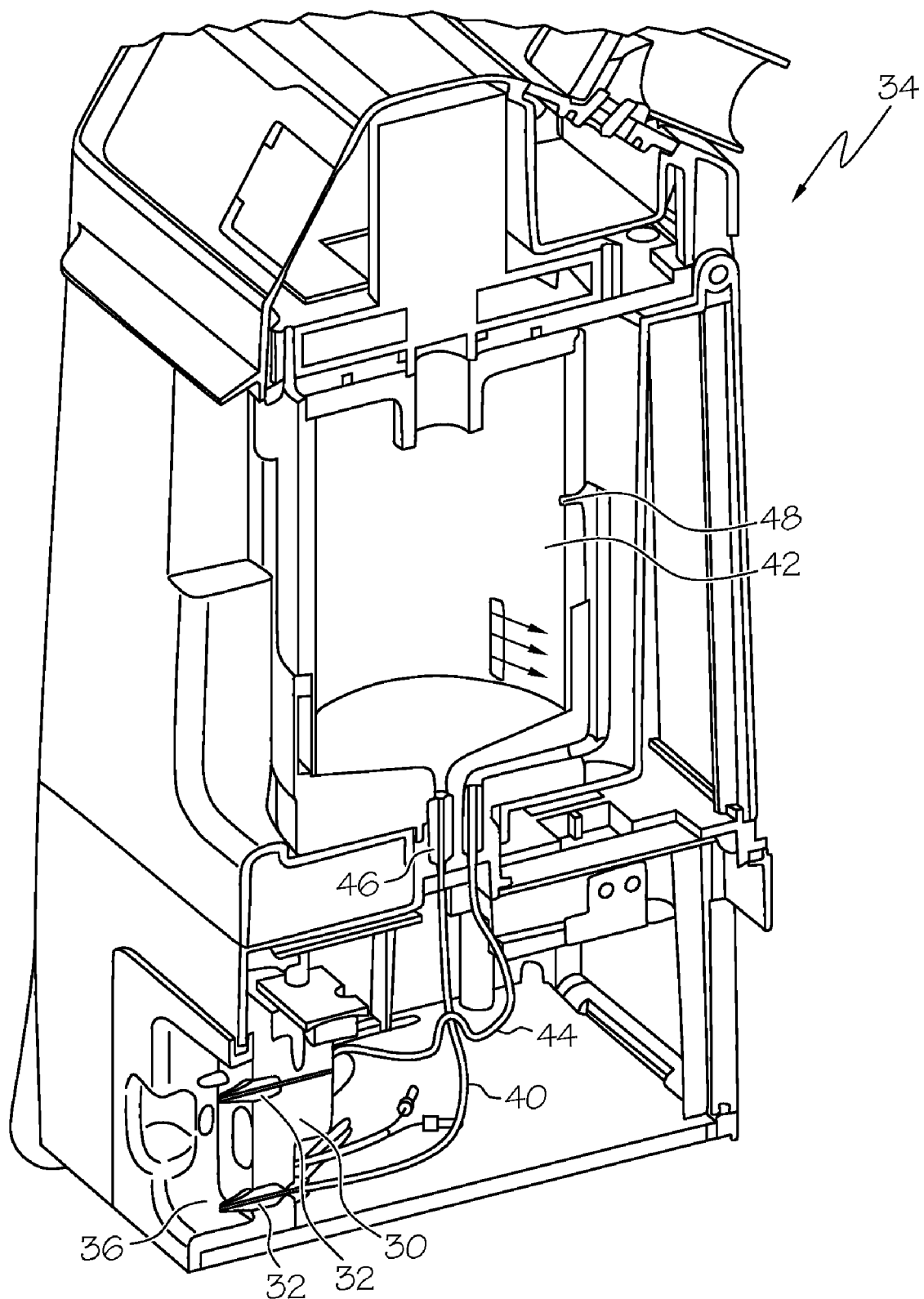
FIG. 4 is a cross-section of a perspective view of an exemplary air and gas sampling device adapted for use with a sampling cartridge according to the present invention.

FIG. 4 is a cross-sectional view of an exemplary air and gas sampling device 34 for which the sample cartridge 10 shown in FIGS. 1-3 is adapted to be used. Manifold 30 is shown in the figure, as are manifold pins 32. Device 34 includes a bay 36 adapted to receive sample cartridge 10. In order to place sample cartridge 10 in operational position within device 34, sample cartridge 10 is inserted such that valves 18 of sample cartridge 10 line up with manifold pins 32 of device 34. Once sample cartridge 10 is in place, device 34 is ready for use. In some embodiments of the present invention, a protective door may be provided over bay 36 such that internal components of device 34 are protected when sample cartridge 10 is not in place.

As can be seen in FIG. 4, sample cartridge 10, once in position, is in communication with a contactor 42 of device 34 by way of manifold 30 and manifold pins 32, which communicate with valves 18a, 18b, and 18c of sample cartridge 10. For example, line 40 provides fluid communication between a lower manifold pin 32 and a fluid inlet 46 of contactor 42. Likewise, line 44 provides fluid communication between an upper manifold pin 32 and an opening 48 positioned above a fluid level in contactor 42. A second upper manifold pin (not shown) may provide fluid communication with either an internal pump (not shown) of device 34, or an external pump adapted to be used with device 34.

In aspects of the present invention having a valve 18c, wherein an upper manifold pin 32 is in fluid communication with a contactor of the air and gas sampling device, the communication between upper manifold pin 32 (and therefore an upper air space within sample cartridge 10) and contactor 42 of the air and gas sampling device combines with the pressure caused by the fluid in the contactor to create a pressure balance that allows fluid to gradually flow out of sample cartridge 10 and into the contactor to replace fluid that evaporates from the contactor. In such an aspect of the present invention, a sensor may also be provided to monitor the fluid level in sample cartridge 10 such that additional fluid may be pumped into sample cartridge 10 via a pump in communication with an upper manifold pin 32, either from a fluid reservoir included in the air and gas sampling device or from some source external to the air and gas sampling device. Thus, sample cartridge 10 can be provided with a continuous source of fluid, enabling long-term, continuous operation of the sampling device.

In addition to the aspects of the present invention described above, sample cartridge 10 may be provided with an integral memory device that can receive and record data, such as the lot number of a particular cartridge, the date of manufacture thereof, collection date of the sample, run time, flow rates, collection fluid type, ambient temperature, humidity, occurrence of system alarms, and the like. Such a memory device could include a magnetic storage device, a flash storage device, a RAM storage device, a computer-readable disc storage device, other devices, or any combination of the foregoing, and may be molded into the structure of sample cartridge 10 or otherwise affixed thereto. A transmission or receiving portion may be included into the air and gas sampling device such that the device may communicate information to sample cartridge 10, or may receive information therefrom. Such transmission or receiving of communications may occur via, for example, radio frequency, or by any other suitable methods of transmitting or receiving data. In addition to a data storage device, an identifier may be included with the present sample cartridge, the identifier simply providing identifying information that may subsequently be associated with specific data regarding a sample contained within the sample cartridge. The identifier may be a human-readable identifier, such as, for example, a serial number printed on the cartridge, or may be a computer-readable identifier such as, for example, a bar code or RFID device.

Figure 5:
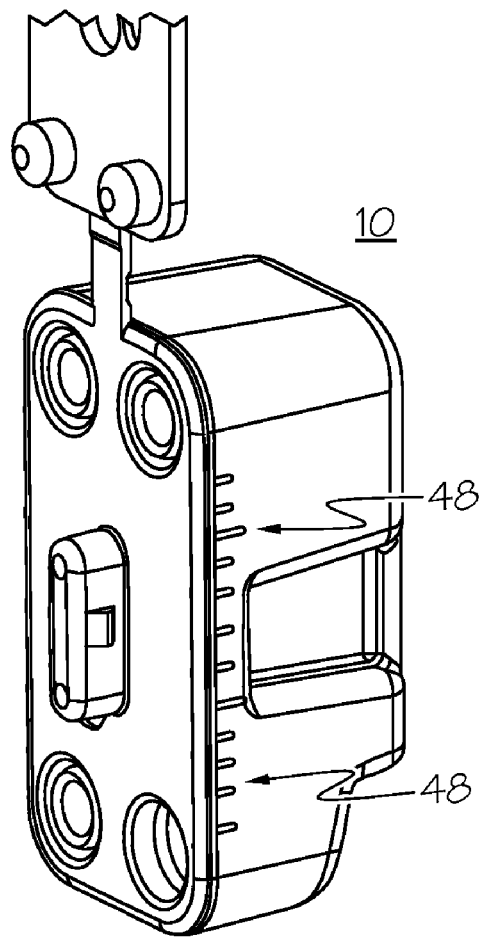
FIG. 5 is a perspective view of one embodiment of a sample cartridge constructed in accordance with the teachings of the present invention.
Figure 6:
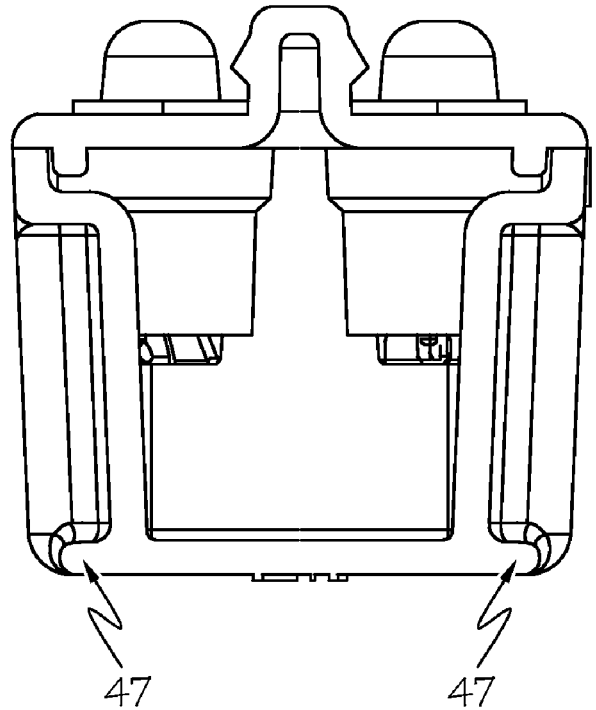
FIG. 6 is a cross-sectional view of one embodiment of a sample cartridge constructed in accordance with the teachings of the present invention.

FIGS. 5 and 6 illustrate additional features that may be included with some embodiments of sample cartridge 10. FIG. 5 is a perspective view of one embodiment of a sample cartridge constructed in accordance with the teachings of the present invention, illustrating gauge marks 48 that may be molded into the surface of sample cartridge 10, allowing for a quick and easy estimate of the sample volume therein. Any suitable markings may be used to allow for estimation of the volume of a sample or other fluid within sample cartridge 10.

FIG. 6 provides a cross-sectional view of sample cartridge 10, and shows molded ribs 47, which allow for a user's fingers to securely grip sample cartridge 10 when using gloves or other hand-protective gear, and also allows for easy insertion of sample cartridge 10 into an air and gas sampling device, as well as easy removal therefrom. Any suitable gripping portion may be used to allow easy manipulation of cartridge 10.

Each of the various components of sample cartridge 10 may be constructed from a variety of materials, as will be readily apparent to those of skill in the art upon reading this disclosure. Materials may be selected, for example, according to weight, durability, insulating qualities, and the like. In addition, materials may be selected according to chemical compatibility with chemicals or agents likely to come into contact with sample cartridge 10 during use.

The specific embodiments of the present invention described above are provided by way of example only, and are not meant to limit the subject matter of the present invention. Various alterations and modifications to the above will be apparent to those of skill in the art upon reading this disclosure. For example, the number, configuration, arrangement, and type of valves may be varied without departing from the spirit or scope of the present invention. Likewise, the size, shape, and configuration of sample cartridge 10, as well as the mechanism by which sample cartridge 10 associates with a gas and air sampling device, may be varied. The present invention is limited only by the claims that follow.

The invention claimed is:

1. A sample cartridge for use with an air and gas sampling device comprising:
a cartridge body, adapted to hold a fluid sample, having at least one self-sealing sample access valve adapted to allow bidirectional fluid communication between the sample and an exterior device; the at least one self-sealing sample access valve having a resilient opening, in a normally sealed orientation, that is adapted to exert a constant radially-inward compressive force; the at least one self-sealing sample access valve being capable of operatively engaging an air and gas sampling device for allowing bidirectional fluidic flow communication between the cartridge body and the air and gas sampling device, whereupon disengagement, the constant radially-inward compressive force causes the resilient opening to automatically seal and return to the normally sealed orientation for preventing fluid communication.

2. The sample cartridge according to claim 1 further comprising a cap portion that is removably engaged with the sample cartridge; wherein the cap portion is adapted to form a seal against the at least one self-sealing sample access valve.

3. The sample cartridge according to claim 1 further comprising a data storage apparatus for storing data related to a sample contained within the cartridge.

4. The sample cartridge according to claim 3 wherein the data storage apparatus is selected from the group consisting of magnetic storage devices, flash storage devices, computer-readable discs, RFID devices, RAM storage devices, and combinations thereof.

5. The sample cartridge according to claim 3 further comprising a data communication device for transmitting and receiving data to and from the air and gas sampling device.

6. The sample cartridge according to claim 1 wherein the sample cartridge is a single-use, disposable sample cartridge.

7. The sample cartridge according to claim 1 wherein the sample cartridge is pre-charged with a sampling fluid contained within the cartridge body.

8. The sample cartridge according to claim 1 wherein the sample cartridge is adapted to receive a fluid sample after the fluid sample has been processed by the air and gas sampling device.

9. The sample cartridge according to claim 1 further comprising at least one gripping portion on an exterior surface of the cartridge body, the gripping portion allowing for easy manipulation of the sample cartridge by a user thereof.

10. The sample cartridge according to claim 1 further comprising a plurality of markings on an exterior surface of the cartridge body, the markings adapted such that a user of the sample cartridge can use the markings to estimate a volume of fluid within the sample cartridge.

11. The sample cartridge according to claim 1 further comprising a sterilization indicator attached to the cartridge body.

12. The sample cartridge according to claim 1 further comprising a sensor for monitoring the level of a fluid contained within the cartridge body.

13. The sample cartridge according to claim 1 further comprising an identifier for identifying a sample contained within the sample cartridge.

14. The sample cartridge according to claim 13 wherein the identifier is machine-readable or computer-readable.

15. A sample cartridge for use with an air and gas sampling device comprising:
a cartridge body having an interior void therein; and
a plurality of self-sealing sample access valves seated in the cartridge body that are in fluid communication with the interior void, allowing bidirectional fluid communication between a sample and an exterior device, wherein each of the plurality of self-sealing sample access valves has a resilient aperture; the resilient aperture defining a generally-conical body member having an axial conduit in communication with a first axial opening and a second axial opening; the axial conduit having a proximal end in communication with the first axial opening and a distal end in communication with the second axial opening wherein the axial conduit has a diameter adapted to narrow from a widest diameter at the proximal end to a minimal diameter at the distal end, such that the axial conduit is sealed at the distal end in a normally sealed orientation; the generally-conical body member of the resilient aperture being adapted to exert a radially-inward compressive force in order to compress and seal the distal end of the axial conduit with the first axial opening being capable of mating with a sample interface pin of the air and gas sampling device;
the generally-conical body member of the resilient aperture being further adapted to acquire an open orientation when operatively engaged with the sample interface pin and allow the sample interface pin to traverse the resilient aperture and fluidly communicate with the interior void, thus allowing bidirectional fluidic flow communication between the interior void and the air and gas sampling device; wherein the open orientation of the generally-conical body member of the resilient aperture elastically-conforms to the sample interface pin and exerts the radially-inward compressive force in order to maintain a seal about the sample interface pin;
wherein, upon operative disengagement from the sample interface pin, the generally conical body member of the resilient aperture continues to exert a radially-inward compressive force in order to compress and automatically return the distal end of the axial conduit to the normally sealed orientation.

16. The sample cartridge according to claim 15 further comprising a cap portion that is removably engaged with the sample cartridge, wherein the cap portion is adapted to form a seal against at least one of the a plurality of self-sealing sample access valves.

17. The sample cartridge according to claim 15 further comprising a data storage apparatus for storing data related to a sample contained within the cartridge.

18. The sample cartridge according to claim 17 wherein the data storage apparatus is selected from the group consisting of magnetic storage devices, flash storage devices, computer-readable discs, RFID devices, RAM storage devices, and combinations thereof.

19. The sample cartridge according to claim 17 further comprising a data communication device for transmitting and receiving data to and from the air and gas sampling device.

20. The sample cartridge according to claim 15 wherein the sample cartridge is a single-use, disposable sample cartridge.

21. The sample cartridge according to claim 1 wherein said sample cartridge is pre-charged with a sampling fluid contained within the cartridge body.

22. The sample cartridge according to claim 1 wherein the sample cartridge is adapted to receive a fluid sample after the fluid sample has been processed by the air and gas sampling device.

23. The sample cartridge according to claim 15 further comprising at least one gripping portion on an exterior surface of the cartridge body, the gripping portion allowing for easy manipulation of the sample cartridge by a user thereof.

24. The sample cartridge according to claim 15 further comprising a plurality of markings on an exterior surface of the cartridge body, the markings adapted such that a user of the sample cartridge can use the markings to estimate a volume of fluid within the sample cartridge.

25. The sample cartridge according to claim 15 further comprising a sterilization indicator attached to the cartridge body.

26. The sample cartridge according to claim 1 further comprising a sensor for monitoring the level of a fluid contained within the cartridge body.

27. The sample cartridge according to claim 15 further comprising an identifier for identifying a sample contained within the sample cartridge.

28. The sample cartridge according to claim 27 wherein the identifier is machine-readable or computer-readable.

29. The sample cartridge according to claim 1 further comprising a material contained within the sample cartridge to facilitate the analysis of a sample introduced into the sample cartridge.

30. The sample cartridge according to claim 15 further comprising a material contained within the sample cartridge to facilitate the analysis of a sample introduced into the sample cartridge.

31. An air and gas sampling system comprising:
an air and gas sampling device for analyzing a sample, adapted to operatively engage a sample cartridge, and further adapted to store the sample therein;
the air and gas sampling device having at least one sample interface pin adapted for operatively engaging the sample cartridge through a plurality of self-sealing sample access valves, the sample interface pin capable of bidirectional fluid flow communication with the sample contained within the sample cartridge in order to transfer the sample into the air and gas sampling device; and
wherein each of the plurality of self-sealing sample access valves has a resilient aperture with the resilient aperture defining a generally-conical body member having an axial conduit in communication with a first axial opening and a second axial opening; the generally-conical body member of the resilient aperture adapted to exert a radially-inward compressive force in order to compress and seal the second axial opening of the axial conduit; the generally-conical body member being adapted for operatively mating with the at least one sample interface pin;
wherein, upon operative disengagement with the at least one sample interface pin, the generally conical body member of the resilient aperture continues to exert a radially-inward compressive force in order to compress and seal the second axial opening of the axial conduit.

32. The air and gas sampling system claim 31, wherein the air and gas sampling device is capable of retaining a portion of the sample for further analysis.

* * * * *